United States Patent
Yoshida et al.

(10) Patent No.: US 6,590,134 B1
(45) Date of Patent: Jul. 8, 2003

(54) PAD, PRODUCTION METHOD THEREFOR, AND EMERGENCY ADHESIVE PLASTER USING THE PAD

(75) Inventors: Takeshi Yoshida, Sukagawa (JP); Yasushi Mashiko, Sukagawa (JP)

(73) Assignee: Johnson & Johnson Kabushiki Kaisha (JP)

( * ) Notice: Subject to any disclaimer, the term of this patent is extended or adjusted under 35 U.S.C. 154(b) by 0 days.

(21) Appl. No.: 09/600,791

(22) PCT Filed: Dec. 10, 1999

(86) PCT No.: PCT/JP99/06938

§ 371 (c)(1), (2), (4) Date: Jan. 18, 2002

(87) PCT Pub. No.: WO00/35393

PCT Pub. Date: Jun. 22, 2000

(30) Foreign Application Priority Data

Dec. 11, 1998 (JP) .............................. 10-353453

(51) Int. Cl.$^7$ ................................. A61F 13/00
(52) U.S. Cl. ............................ 602/43; 602/45
(58) Field of Search ............... 602/41–47, 53, 602/54, 56

(56) References Cited

U.S. PATENT DOCUMENTS

| 3,885,559 A | 5/1975 | Economou |
| 4,622,089 A | 11/1986 | Lauritzen |
| 5,328,450 A | 7/1994 | Smith |

FOREIGN PATENT DOCUMENTS

| EP | 0 353 972 A1 | 2/1990 |
| EP | 0 676 183 A1 | 10/1995 |
| GB | 831963 | 4/1960 |
| GB | 925580 | 5/1963 |
| GB | 2 249 266 A | 5/1992 |
| JP | 62-15329 U | 1/1987 |
| JP | 64-37227 U | 3/1989 |
| JP | 2-182259 A | 7/1990 |
| JP | 3-244456 A | 10/1991 |
| WO | WO 89/05133 A1 | 6/1989 |
| WO | WO 97/42917 A1 | 11/1997 |

OTHER PUBLICATIONS

European Patent Office Search Report issued Apr. 20, 2001 in corresponding EPO Patent Application No. 99 12 4011.
International Search Report issued Mar. 21, 2000 (21.03.00) in corresponding PCT Patent Application No. PCT/JJ99/06938.

Primary Examiner—Nicholas D. Lucchesi
Assistant Examiner—Lalita M. Hamilton

(57) ABSTRACT

A pad comprising an approximate-quadrangular portion and approximate-arched portions attached to both lateral sides of the approximate-quadrangular portion and all the periphery of said pad is sealed with ultrasonic treatment wherein: when L represents the length of the approximate-quadrangular portion in the direction parallel to the lateral axis, S represents the length of the approximate-quadrangular portion in the direction parallel to the vertical axis and R represents a radius of said approximate-arched portion, following relations are satisfied: $0.5S \leq L \leq 4S$ between L and S; $0.5S \leq R < S$ between S and R, the production method and the adhesive bandage using said pad. The pad prevents peeling-off from four corners thereof and intrusion of water.

3 Claims, 5 Drawing Sheets

PAD, PRODUCTION METHOD THEREFOR, AND EMERGENCY ADHESIVE PLASTER USING THE PAD

TECHNICAL FIELD

This invention relates to a pad, a production method thereof and adhesive bandage using said pad.

TECHNICAL BACKGROUNDS

Conventionally, fiber cluster or nonwoven fabric made of natural fiber such as cotton and synthetic fiber such as rayon having quadrangular shape by cutting vertical and lateral straight lines has been used as it is for a pad, especially for a pad of an adhesive bandage for absorbing body liquid and for protecting wound. Further pads using such fabrics as pad materials and being covered with a film or net of plastics such as polyethylene for preventing such pad materials to stick to the wound or for avoiding irritation are conventionally used. For the covering method, two-direction holding and four-direction holding are known. FIG. 1 is an example of a pad for an adhesive bandage of a known shape, which uses as a pad a rectangular nonwoven fabric made by cutting vertical and lateral straight lines.

In such pads having such as square or rectangular shape, when being used for an adhesive bandage, a strength concentrates in the four edges of the pad on the backing sheet of the adhesive bandage because of the pad thickness, and leak arises from the edges, and also the backing sheet tends to be peeled or stripped off from skin. And in the case of the pad covered with a polymer net, when holding the pad in two directions out of four directions, there is leak or projection of fibers constructing the pad in two directions not held, which is not preferred for appearance, and in the case of four-directional holding, the manufacturing process becomes complicated, the price expensive and productivity decreased, consequently holding a part of the polymer net periphery is usually adopted.

DISCLOSURE OF THE INVENTION

This invention relates to a pad comprising an approximate-quadrangular portion and approximate-arched portions attached to both lateral sides of the approximate-quadrangular portion and all the periphery of said pad is sealed with ultrasonic treatment wherein:

when L represents the length of the approximate-quadrangular portion in the direction parallel to the lateral axis, S represents the length of the approximate-quadrangular portion in the direction parallel to the vertical axis and R represents a radius of said approximate-arched portion, following relations are satisfied:

$0.5S \leq L \leq 4S$ between $L$ and $S$ $0.5S \leq R < S$ between $S$ and $R$.

The pad having such shape may provide comfortable use feeling without decrease in liquid absorbability, no leak of fibers from four sides, and make it possible to simplify the manufacturing processes and improve productivity and decrease in product defective ratio.

A size of the pad may be appropriately selected according to the shape, range, length, etc. of a wound the pad is applied to. However when L represents the length of the approximate-quadrangular portion in the direction parallel to the lateral axis and S represents the length of the approximate-quadrangular portion in the direction parallel to the vertical axis, L and S should satisfy following relation: $0.5S \leq L \leq 4S$. When the L is no more than 0.5S, it is not preferred because the length of the lateral direction of the adhesive bandage cannot be made long enough when using an adhesive bandage. When L exceeds 4S, the pad is too thin to absorb body liquid if a large amount of body liquid is flown out of the wound, and not preferred. Further when considering the pad of this invention covers a wound to absorb a large amount of body liquid, it is preferred to satisfy following relation; $0.9S \leq L \leq 1.45S$.

In the pad of this invention, above R and S may be in the following relation: $0.5S \leq R < S$. When R is no more than 0.5S, a diameter of said approximate-arched portion becomes smaller than the vertical length of the approximate-quadrangular portion, the peripheral curve of the pad cannot be smoothed. When more than S, the arc of the approximate-arched portion is too straight, and not preferred. In the pad of this invention if attaining effective absorption of body liquid oozing, the relations of following formulas:

$$0.55S \leq R \leq 0.9S \text{ in particular } 0.6S \leq R \leq 0.8S$$

is preferred. In order to smooth the peripheral shape of the pad, the corners of the pad are preferably rounded. FIG. 2 shows the relationships of S, L and R.

The whole periphery of the pad of this invention is sealed by such as an ultrasonic heating. By sealing whole periphery, leak of fiber ends from four sides of the pad may be almost perfectly prevented. In ultrasonic heating, the heat is generated only when the ultrasound is insonified and the product yield ratio and safety are improved, high-speed operation is possible and ultrasonic heating is also preferred in view of productivity improvement and miniaturization of the facilities. Further to reduce the facility cost, electric-heat-seal may be adopted instead of the ultrasonic-heat seal.

When sealing the whole periphery as said above, sealed portion can be thinner than unsealed portion, further thickness may be gradually changed from central unsealed portion to the periphery further to adhesive layer of the adhesive bandage. Thereby a smooth thickness change from unsealed portion toward the periphery is attained if the unsealed portion is made thick, and peeling of the adhesive bandage may be prevented.

The material of the pad is not particularly restricted as far as the material has a proper elasticity and liquid absorbability, and clusters of fibers or nonwoven fabrics of natural fibers, synthetic fibers may be used, nonwoven fabrics are preferred among them because bulkiness may be controlled and liquid absorbability may be increased. As the natural fibers, cotton, silk cotton, and synthetic fibers, polyethylene, polypropylene, polyesters and rayon can be used. Synthetic fibers are preferred because they are heat-sealable and easy to handle, especially the material of the pad preferably includes more than two kind of filaments composed of one or more than two materials selected from the group consisting of rayon, polyethylene, polyesters and polypropylene. Further mixture of two or more than three kinds of filaments can be used. Hydrophilic fibers such as hydrophilic polyesters, further water-absorbable polymer particles may be mixed to improve liquid absorbability. When rayon is used to improve liquid absorbability, the content of the rayon can be 30 to 60%, if less than 30%, expected effects by mixing the rayon cannot be attained. A preferable heat-sealability may not be attained when rayon exceeds 60%.

The outside surface of the pad may be covered with such as polymer fabric, nonwoven fabric or nets or films. The polymer net is preferred because of operability in the heat-seal process. By covering the outside surface of the pad material with polymer net, a pad form is retained, scattering of the pad material filaments is prevented, further direct contact of the pad material to wound or fixing of the pad to the wound may be prevented. The polymer for the polymer net materials are not in particular restricted, however polyolefines such as polyethylene, polypropylene, polyester such as polyethylene terephthalates and polybutylene telephthalates, nylons, etc. are preferred. Polyethylene is in particular preferred because of handleability, peelability from wound, safety and so forth.

When the pad of this invention is manufactured using nonwoven fabric as a pad material and a polymer net as covering material, seal and cut of the pad and polymer net can be performed simultaneously. By performing the processes at a time, they may be simplified, the displacement between the seal portion and the cutting line as well as production of off-specification products is prevented, product yield ratio is improved. Further simultaneous process is preferable in view of working efficiency. Especially it is preferred to perform seal and cut simultaneously by ultrasonic-heating, however the process can be; firstly sealing the nonwoven fabric and polymer net by ultrasonic-heating, then cutting the periphery of the sealed portion by ultrasonic-heating. Further a method can be adopted where point-sealing the nonwoven fabric and polymer net at a number of point on the pad surface, sealing the periphery thereof, then cutting the periphery of the sealed portion by the ultrasonic-heating.

A pad of this invention includes all the devices which may protect wounds such as operation wounds, external wounds and skin affections from external stimulation, decrease annoyance of wounds by, absorbing body liquid such as blood from the wound, and accelerate cure. The pad may be used independently, further widely used for bandages, adhesive bandages, dressings, wound-dressings, in particular used for pads of adhesive bandages.

BEST MODE FOR CARRYING OUT THE INVENTION

Figure 1:
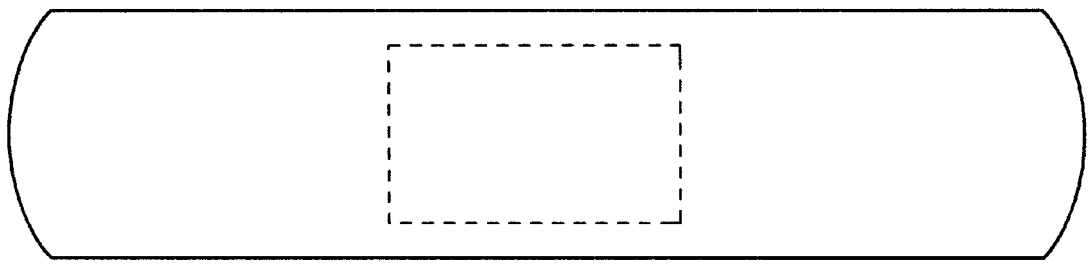
FIG. 1 is an example of a conventional adhesive bandage.
Figure 2:
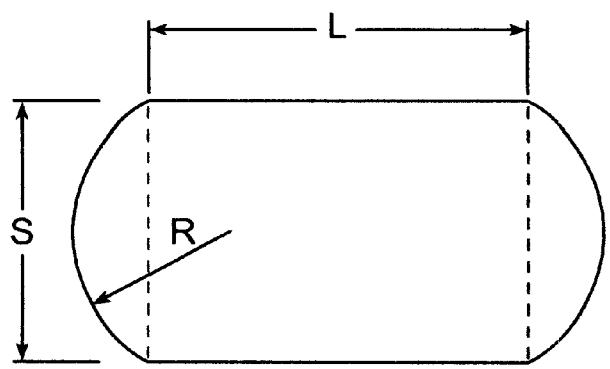
FIG. 2 is a periphery of an example of a pad of the present invention.
Figure 3:
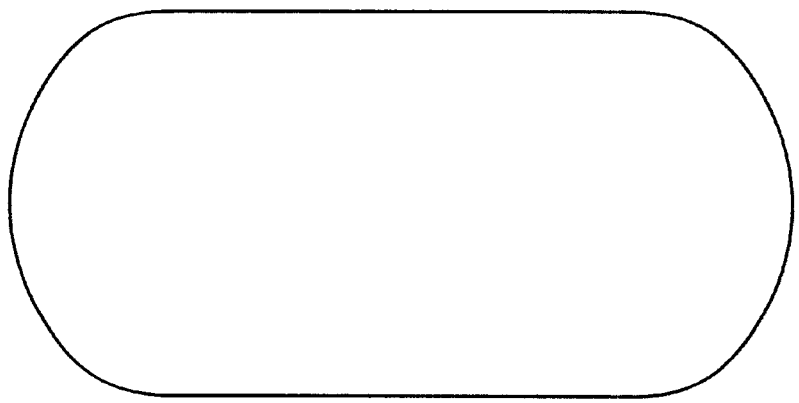
FIG. 3 is an example of a pad of which four corners in FIG. 2 are rounded.
Figure 4:
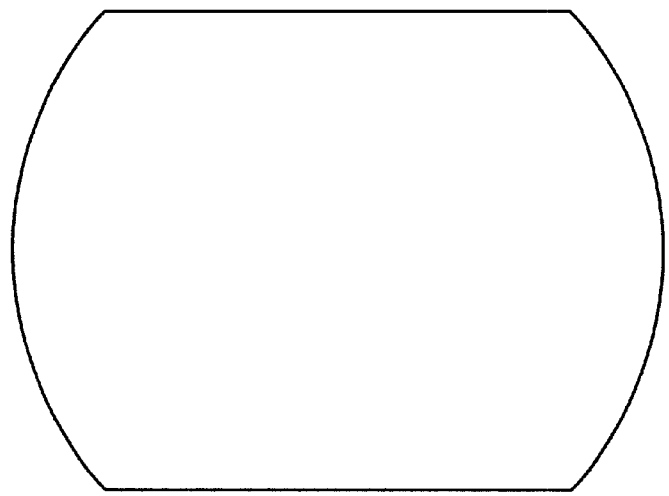
FIG. 4 is another example of the present invention.
Figure 5:
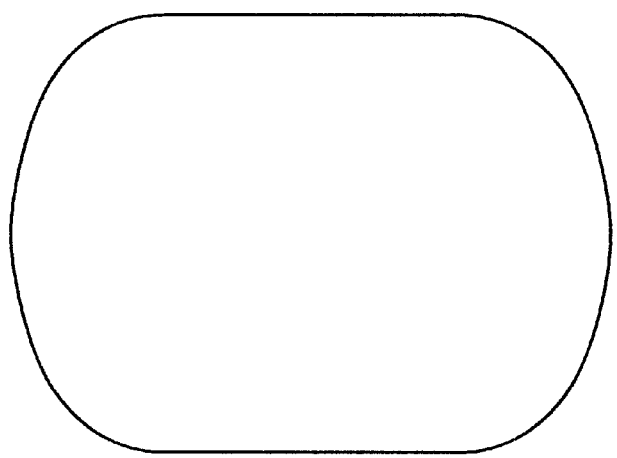
FIG. 5 is an example of a pad of which four corners of the pad of FIG. 4 are rounded.
Figure 6:
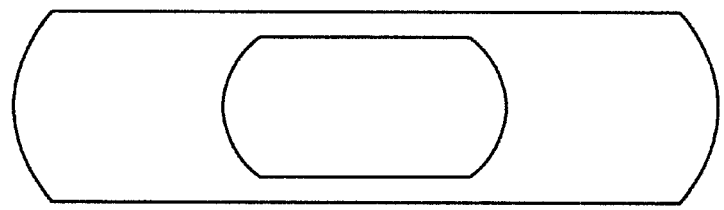
FIG. 6 is an example of an adhesive bandage using the pad of FIG. 2.

FIG. 2 shows a periphery of an example of this invention. The approximate-quadrangular portion is shown by a rect-angle enclosed by straight line of the pad periphery and dotted lines inside the pad, and the arched portions are shown by the areas attached to both right and left sides of the approximate-quadrangular portion. The length of the straight line is shown by L, and that of the dotted line, by S. The radius of the arch of the arched portion is represented by R. In this example, the ratio of L/S is 1.5 and R/S is 0.7. FIG. 2 is made up of straight lines and circular arcs, FIG. 3 is an example of the pad in FIG. 2 of which four corners are rounded. FIG. 4 shows an example when L/S is 1.0 and R/S is 0.7, and FIG. 5 shows an example when four corners of the example in FIG. 4 are rounded. FIG. 6 shows an example when the pad of this invention shown in FIG. 2 is put to use for an adhesive bandage. Comparing to the conventional adhesive bandage shown in FIG. 1, the adhesive bandage is difficult to peel off when it is applied because angles of corners of the pad periphery are small, the adhesive bandage can prevent intrusion of outside water during bathing or washing.

Figure 7:
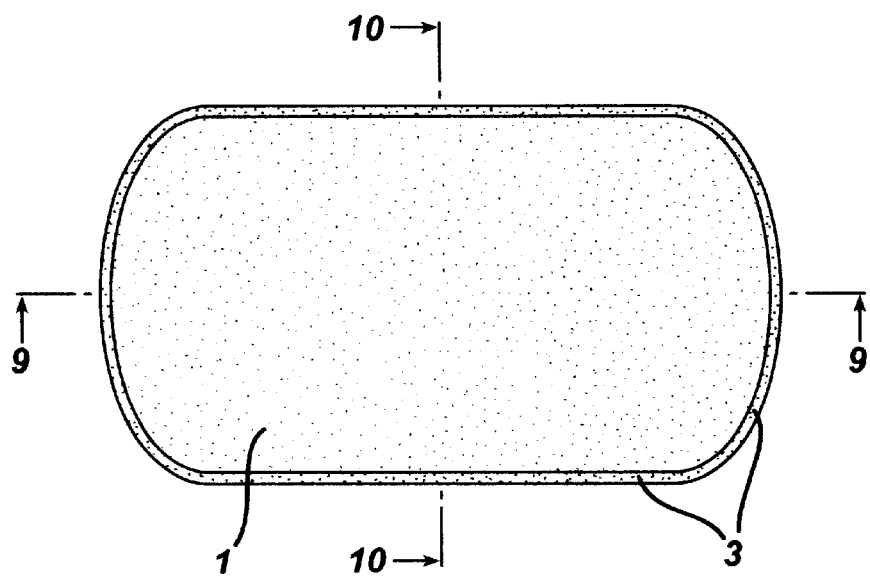
FIG. 7 is an example of which pad periphery is sealed and cut by ultrasonic heating.
Figure 8:
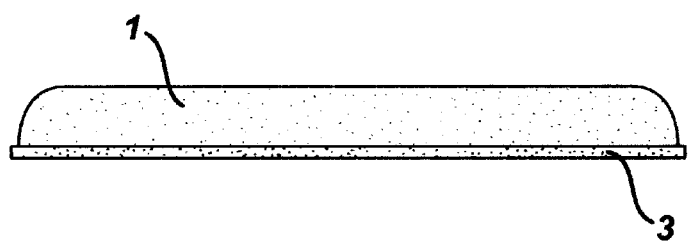
FIG. 8 is a front view of the example in FIG. 7.
Figure 9:
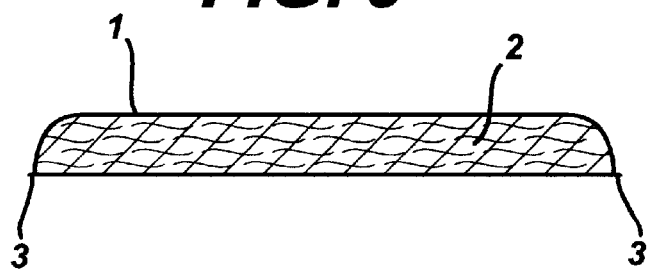
FIG. 9 is a sectional view along B—B line in FIG. 7.
Figure 10:
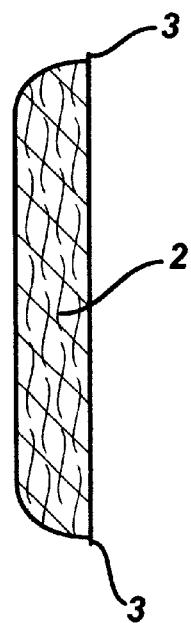
FIG. 10 is a sectional view along A—A line in FIG. 7.

FIG. 7 shows a plane view of an example sealing and cutting the periphery of the pad in the shape shown in FIG. 3 by ultrasonic heating. The sealed portion (3) is allocated whole periphery of the pad. FIG. 8 shows an elevation view of this example. The unsealed portion is several times thicker than the sealed portion. The sectional view of B—B section in FIG. 7 is shown in FIG. 9, and its side view in FIG. 10. No leak of fibers can be seen on the pad sealed by ultrasonic heating.

Figure 11:
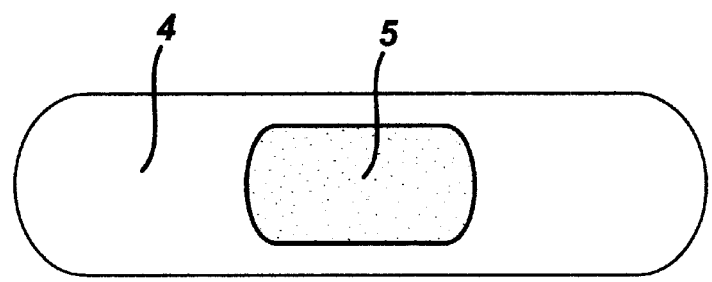
FIG. 11 is a plane view of an adhesive bandage using the pad in FIG. 7.
Figure 12:
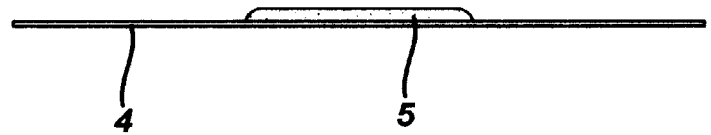
FIG. 12 is a front view of the adhesive bandage in FIG. 11.

FIG. 11 is a plane view of an adhesive bandage using the pad shown in FIG. 7, and FIG. 12 a front view thereof.

Figure 13:
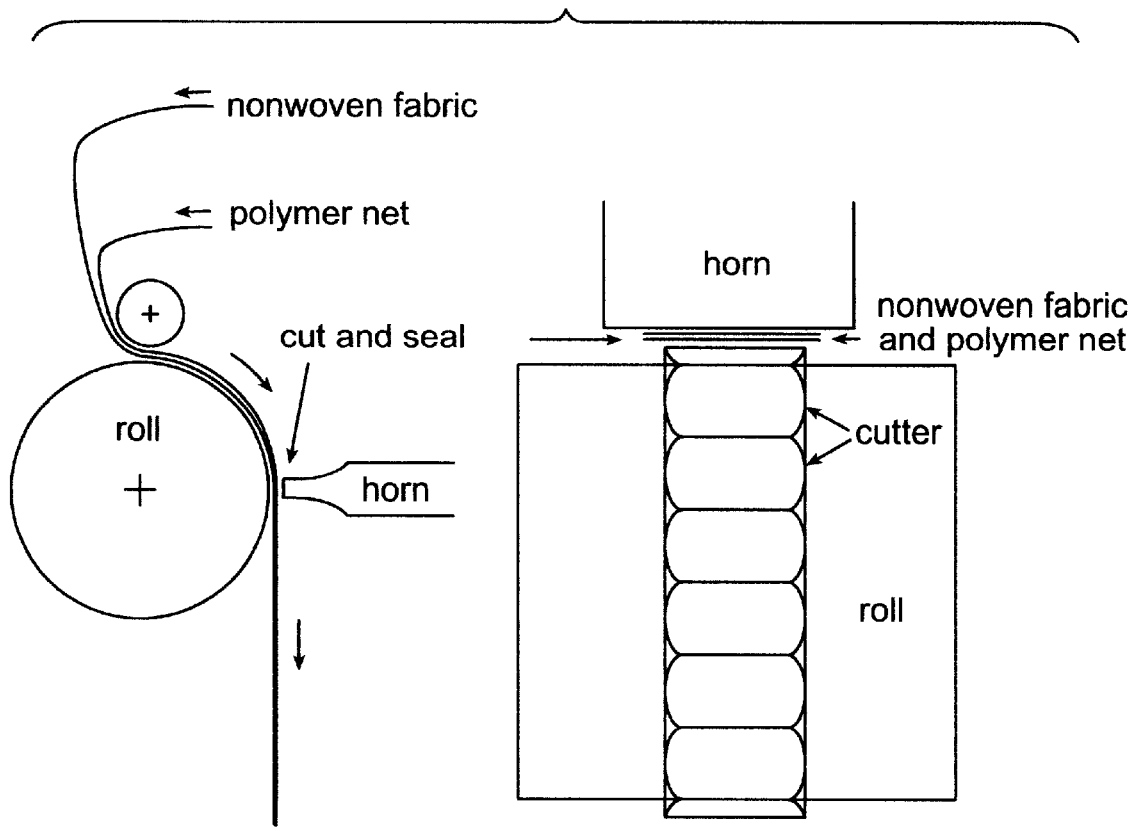
FIG. 13 is a schematic view of a machine performing sealing and cutting by ultrasonic heating. As to description of symbols, 1 is a pad, 2 is a nonwoven fabric, 3 is a sealed portion, 4 is a backing sheet of adhesive bandage.

FIG. 13 is a schematic view of a machine performing sealing and cutting of a periphery of a pad of this invention by ultrasonic heating. A nonwoven fabric and polymer net is separately sent from above, laminated by supporting roll and pass between a horn of a ultrasound generator and a roll. The nonwoven fabric and polymer net are heated by ultrasound vibration, sealed, cut and then a pad is formed.

A point-sealing device can also be attached to between the supporting roll and the roll for ultrasound generator so as to point-seal the pad surface in proper distance and distribution.

INDUSTRIAL APPLICABILITY

The pad provides comfortable use feeling without decrease in liquid absorbability, no leak of fibers from four sides, and makes it possible to simplify the manufacturing processes and improve productivity and decrease in product defective ratio. When using for adhesive bandage especially, peel-off of the pad from four corners of the pad and intrusion of outside water can be prevented.

What is claimed is:

1. A production method of a pad comprising an approximate-quadrangular portion and approximate-arched portions attached to both lateral sides of the approximate-quadrangular portion made up with a nonwoven fabric and the surface of said pad being covered with a polymer net; and when L represents the length of the approximate-quadrangular portion in the direction parallel to the lateral axis, S represents the length of the approximate-quadrangular portion in the direction parallel to the vertical axis and R represents a radius of said approximate-arched portion, following relations are satisfied:

$0.5S \leq L \leq 4S$ between $L$ and $S$ $0.5S \leq R < S$ between $S$ and $R$, wherein the nonwoven fabric and the polymer net of the whole periphery of said pad are sealed and cut simultaneously by ultrasonic heating.

2. A production method of a pad comprising an approximate-quadrangular portion and approximate-arched portions attached to both lateral sides of the approximate-quadrangular portion made up with a nonwoven fabric and the surface of said pad being covered with a polymer net; and when L represents the length of the approximate-quadrangular portion in the direction parallel to the lateral axis, S represents the length of the approximate-quadrangular portion in the direction parallel to the vertical axis and R represents a radius of said approximate-arched portion, following relations are satisfied:

$0.5S \leq L \leq 4S$ between $L$ and $S$ $0.5S \leq R < S$ between $S$ and $R$, wherein the nonwoven fabric and the polymer net of the whole periphery of said pad is sealed by ultrasonic heating, and then the sealed peripheral portion is cut by ultrasonic heating.

3. A production method of a pad comprising an approximate-quadrangular portion and approximate-arched portions attached to both lateral sides of the approximate-quadrangular portion made up with a nonwoven fabric and the surface of said pad being covered with a polymer net; and when L represents the length of the approximate-quadrangular portion in the direction parallel to the lateral axis, S represents the length of the approximate-quadrangular portion in the direction parallel to the vertical axis and R represents a radius of said approximate-arched portion, following relations are satisfied:

$0.5S \leq L \leq 4S$ between $L$ and $S$ $0.5S \leq R < S$ between $S$ and $R$, wherein the nonwoven fabric and the polymer net on the pad surface are point-sealed, then the nonwoven fabric and the polymer net of the whole periphery of said pad is sealed by ultrasonic heating, and then the sealed peripheral portion is cut by ultrasonic heating.

* * * * *